US011513106B2

(12) United States Patent
Folli et al.

(10) Patent No.: US 11,513,106 B2
(45) Date of Patent: Nov. 29, 2022

(54) APPARATUS AND METHOD FOR AUTOMATICALLY DETECTING ODORANT SUBSTANCES IN SOLUTION BY USING NEMATODES CAENORABDITIS ELEGANS (71) Applicants: FONDAZIONE ISTITUTO ITALIANO DI TECNOLOGIA, Genoa (IT); DISRUPTIVE TECHNOLOGICAL ADVANCES IN LIFE SCIENCES S.R.L., Rome (IT)

(72) Inventors: Viola Folli, Genoa (IT); Andrea Santinelli, Rome (IT); Marco Broglia, Rome (IT)

(73) Assignees: FONDAZIONE ISTITUTO ITALIANO DI TECNOLOGIA, Genoa (IT); DISRUPTIVE TECHNOLOGICAL ADVANCE IN LIFE SCIENCES S.R.L., Rome (IT)

( * ) Notice: Subject to any disclaimer, the term of this patent is extended or adjusted under 35 U.S.C. 154(b) by 342 days.

(21) Appl. No.: 16/756,669

(22) PCT Filed: Oct. 19, 2018

(86) PCT No.: PCT/IB2018/058127
§ 371 (c)(1),
(2) Date: Apr. 16, 2020

(87) PCT Pub. No.: WO2019/077558
PCT Pub. Date: Apr. 25, 2019

(65) Prior Publication Data
US 2020/0333305 A1    Oct. 22, 2020

(30) Foreign Application Priority Data
Oct. 20, 2017  (IT) .................. 102017000119113

(51) Int. Cl.
*G01N 33/00* (2006.01)
*G01N 33/50* (2006.01)
(Continued)

(52) U.S. Cl.
CPC .... *G01N 33/0001* (2013.01); *B01L 3/502761* (2013.01); *G01N 21/6486* (2013.01); *G01N 33/5085* (2013.01); *B01L 2300/0663* (2013.01)

(58) Field of Classification Search
CPC .... G01N 33/00; G01N 33/0001; G01N 33/50; G01N 33/5085; G01N 21/6486; A01K 67/033; B01L 3/502761; B01L 2300/0663
(Continued)

(56) References Cited

U.S. PATENT DOCUMENTS 11,022,607 B2    6/2021  Manivet
2004/0073961 A1  4/2004  Andres et al.
(Continued)

FOREIGN PATENT DOCUMENTS

CN    105164529 A    12/2015
CN    106255877 A    12/2016
(Continued)

OTHER PUBLICATIONS

N. Bakhtina, J. Korvink, "Microfluidic laboratories for C. elegans enhance fundamental studies in biology," RSC Adv., 2014, 4, 4691.
(Continued)

*Primary Examiner* — Terrell H Matthews
(74) *Attorney, Agent, or Firm* — Merchant & Gould P.C.

(57) ABSTRACT

Apparatus (1000) and method for automatically detecting odorant substances based on use of nematodes that includes a mechanical selection unit (100) configured to select nematodes in adult stage from an initial nematode population obtaining an intermediate nematode population, a nematode optical selection unit (200) configured to select from the
(Continued)

intermediate population a final population of nematodes in adult stage and to select nematodes in young adult stage from nematodes in egg producing adult stage to be sent to a measurement unit (300) configured to detect the response of nematodes of the final population to a stimulus of an odorant substance, the mechanical selection unit (100) being connected to the optical selection unit (200) by a connection channel with an at least three way branch and the optical selection unit (200) being connected to the measurement unit (300) by a loading microchannel.

19 Claims, 6 Drawing Sheets

(51) Int. Cl.
*B01L 3/00* (2006.01)
*G01N 21/64* (2006.01)

(58) Field of Classification Search
USPC ..................................................... 250/459.1
See application file for complete search history.

(56) References Cited

U.S. PATENT DOCUMENTS

| 2006/0191023 | A1  | 8/2006 | Gill et al. |
| 2011/0154510 | A1* | 6/2011 | Pak .................... G01N 33/5085 800/12 |
| 2017/0016906 | A1  | 1/2017 | Hirotsu et al. |

FOREIGN PATENT DOCUMENTS

| IT | 201700119113 A1 * | 10/2017 | ........... A01K 67/033 |
| JP | 2021500543 A * | 9/2010 | ......... G01N 33/5085 |
| WO | 2009/021232 A2 | 2/2009 | |
| WO | WO-2019077558 A1 * | 4/2019 | ........... A01K 67/033 |

OTHER PUBLICATIONS

Hirotsu T., et al. "A Highly Accurate Inclusive Cancer Screening Test Using Caenorhabditis elegans Scent Detection, PLoS ONE 10(3): e0118699, doi:10.1371/journal.pone.0118699," (2015).
International Search Report and Written Opinion issued in corresponding application PCT/IB2018/058127, completed Feb. 11, 2019 and dated Feb. 22, 2019.
Chinese Office Action for CN Application No. 201880068024.7 dated Dec. 22, 2021 (9 pages, with English translation).
Chinese Notification of Grant for CN Application No. 201880068024.7 dated Jun. 1, 2022 (3 pages, with English translation).
Japanese Notification of Reasons for Refusal for JP Application No. 2020-521434 dated May 24, 2022 (13 pages, with English translation).
Al et al., "A high-throughput device for size based separation of C. elegans developmental stages," Lab Chip, 2014, 14:1746-1752.

* cited by examiner

APPARATUS AND METHOD FOR AUTOMATICALLY DETECTING ODORANT SUBSTANCES IN SOLUTION BY USING NEMATODES CAENORABDITIS ELEGANS

This application is a National Stage Application of PCT/IB2018/058127, filed Oct. 19, 2018, which claims benefit of Italian Patent Application No. 102017000119113, filed Oct. 20, 2017, and which applications are incorporated herein by reference. To the extent appropriate, a claim of priority is made to each of the above-disclosed applications.

The present invention refers to an apparatus and a method for automatically detecting molecular compounds in solution based on the use of multicellular microorganisms that is efficient, reliable, simple and inexpensive.

In particular, the apparatus is based on the use of nematodes *Caenorhabditis Elegans* or *C Elegans*, highly efficient in recognising and interacting with certain molecular compounds showing high chemo-sensitivity and chemotaxis (phenomenon according to which unicellular or multicellular organisms direct their movements in function of the presence of chemical substances in the surrounding environment). Such molecular compounds interact with the sensorial-olfactory system of the nematodes *C. Elegans*, whereby they are also called odorant substances, or odorants.

The present invention may be applied in different application contexts such as for instance screening in the medical field for early detection of tumour markers and other diseases, control of environmental pollution to detect the presence of certain chemical compounds or toxins, development of artificial intelligence and human-robot interaction through detection of molecules linked to behavioral dynamics, still remaining within the scope of protection defined by the attached claims.

The *C. Elegans* with its genetically modified lineage, the very high efficiency of which in attraction towards specific molecular targets is already known in literature, is naturally capable of a neuronal activity in response to the molecules stimulating its olfactory system. Most of its nervous system and more than 5% of its genes are dedicated to the recognition of chemical substances in the environment. Chemosensory stimuli may induce chemotaxis, change in overall motility and entry and exit from various staged of development. These behaviours are regulated by the sensory organs, amphid, containing 11 pairs of chemo-sensory neurons. Each sensory neuron expresses a specific set of candidate receptor genes and identifies a specific set of attractant molecules, repellent molecules or pheromones. About 500-1000 different G-protein coupled receptors (GPCR) are expressed in the chemo-sensory neurons. Thus *C. Elegans* has a highly developed chemo-sensory system that render the same capable to identify a large variety of volatile or water soluble compounds. In the paper "*Microfluidic laboratories for C. elegans enhance fundamental studies in biology*" by N. Bakhtina, J. Korvink, RSC Adv., 2014, 4, 4691, the authors show that *C Elegans* identifies a large class of molecules, such as for instance sodium chloride NaCl, ethanol, isoamyl alcohol, copper chloride $CuCl_2$, ivermectin, cyanide, glycerol, antibiotics, heavy metals. In Hirotsu T. et al. (2015), A Highly Accurate Inclusive Cancer Screening Test Using Caenorhabditis elegans Scent Detection, PLoS ONE 10(3): e0118699, doi:10.1371/journal.pone.0118699, *C Elegans* sensitivity to tumor metabolites has been shown. With reference to molecules which do not seem so far to stimulate neuronal activity, it is possible to develop a genetically modified variant of the nematode where the necessary receptors are expressed in some of the olfactory sensory neurons. That is, thanks to genetic engineering techniques applied to C. Elegans, it is possible to create transgenic worm lines with high sensitivity to predefined odorants.

Current techniques of identification of odorant substances are based on the measurement of the fluorescence pulse that is generated when the nematode is separated from the stimulus due to the odorant substance under examination (neuronal activity). The main disadvantage is that the nematodes reproduce at high speed and hence also a previously selected population after a few hours will be extremely heterogeneous. The vital stages of *C. Elegans* can be schematized as follows: embryonic stage, 4 larval stages (L1-L4), adult stage. In the adult phase it is possible to distinguish the young adult stage, and the stage of adult starting to produce eggs. The presence of eggs, egg producing adults or individuals close to death (or already dead) involves a very high level of autofluorescence typical of the nematode and thus makes the measurement of the neuronal response particularly complex. Therefore, synchronous nematode rearing with an accuracy of one/two hours compared to the single measurement would be needed, and the detection of compounds is unlikely unrelated to the nematode rearing. The disadvantages described above make an extended and automated use, i.e. from an industrial scale laboratory, of the molecular compound detection techniques based on the use of multicellular microorganisms such as nematodes *C Elegans* difficult.

It is an object of the present invention to overcome the disadvantages described so far, allowing in a reliable, safe and inexpensive way to detect certain molecular compounds by using micro multicellular microorganisms such as nematodes *C. elegans*.

It is specific subject matter of the present invention an automated apparatus for detection of odorant substances based on use of nematodes that includes a mechanical selection unit configured to select nematodes in adult stage from an initial nematode population obtaining an intermediate nematode population, a nematode optical selection unit configured to select from the intermediate population a final population of nematodes in adult stage and to select nematodes in young adult stage from nematodes in egg producing adult stage to be sent to a measurement unit configured to detect the response of nematodes of the final population to a stimulus of an odorant substance, the mechanical selection unit being connected to the optical selection unit by a connection channel with an at least three way branch and the optical selection unit being connected to the measurement unit by a loading microchannel, wherein:

the mechanical selection unit comprises a collection vessel provided with at least one first closable inlet nozzle configured to introduce maintenance buffer liquid containing nematodes into the vessel and at least one second closable inlet nozzle configured to introduce additional buffer liquid into the vessel, wherein the vessel is provided with a closable outlet hole and a motorised double grid, configured to assume a first open configuration and a second closed configuration, wherein said at least one first nozzle and said at least one second nozzle being positioned near a base of the vessel and being configured to fill the vessel starting from the base, the motorized double grid being placed parallel to the base of the vessel at a distance from this greater than said at least one first nozzle and said at least one second nozzle and configured to cause only eggs or larvae of nematodes to pass through its own holes;

the optical selection unit comprises at least three measurement microfluidic channels configured to channel one by one nematodes of the intermediate population, three optical sensors configured to perform a length measurement of the channelled nematodes, an illuminator configured to illuminate the at least three measurement microfluidic channels and that is associated to double photodiodes configured to perform an autofluorescence measurement of the individual channelled nematodes, the optical selection unit being configured to direct a nematode towards the measurement unit or towards a waste tank, and a blocking valve configured to block the passage of nematodes in the measurement unit;

the measurement unit comprises a central layer that includes a microfluidic chip with a pillar microfluidic circuit provided with a loading hole connected to the loading microchannel configured to introduce nematodes into the microfluidic circuit and a drain hole configured to remove nematodes from the microfluidic circuit, the chip being configured to receive a test liquid via a first inlet channel and to receive a neutral buffer liquid via a second input channel, a first end layer including sources configured to emit continuous light and modulated light illuminating the microfluidic circuit, the emitted modulated light being configured to stimulate a fluorescence of nematodes, and the sources being associated with photodiodes configured to receive fluorescence of nematodes, a second end layer including an optical sensor opposite to the first end layer with respect to the central layer, configured to acquire transmitted light images of the microfluidic circuit when it is illuminated by the emitted continuous light and to analyse motility nematodes in presence and in absence of an odorant substance;

the apparatus further comprising a control unit for controlling the mechanical selection unit, the optical selection unit and the measurement unit.

According to another aspect of the invention, said at least three ways of the connection channel and said loading microchannel may have a section not lower than 100 µm.

According to a further aspect of the invention, said holes of the double grid may have a size ranging from 50 um to 500 µm.

According to an additional aspect of the invention, for each of said at least three measurement microfluidic channels said three optical sensors may be positioned along a longitudinal direction of the channel and may be translated from each other at such distances that orthogonal projections on the channel of a first optical sensor, of a second optical sensor and of a third optical sensor identify a first target position, a second target position and a third target position respectively, the second and the third optical sensor being optionally translated with respect to the first optical sensor by about 900 um and 1000 um respectively.

According to another aspect of the invention, with respect to each of said at least three measurement microfluidic channels, each optical sensor may be positioned at a first height and said illuminator at a second height opposite to the first height, said illuminator being positioned in a central position with respect to the three target positions, optionally centrally with respect to the first and second target positions.

According to a further aspect of the invention, said sources of the first end layer may be LEDs arranged in a double array to emit continuous light and modulated light, optionally at 550 nm and at 470 nm respectively, optionally with a modulation frequency not exceeding 1 KHz.

It is further specific subject matter of the present invention a method for automatically detecting odorant substances based on use of nematodes employing the automated detection apparatus of the present invention, the method comprising the following steps:

injecting an initial amount of maintenance buffer liquid containing an initial population of nematodes into the vessel, with said at least one first closable inlet nozzle being open, of the mechanical selection unit through an overpressure system through a microchannel structure, said initial amount of maintenance buffer liquid being such as to touch the double grid in open configuration;

after an interval of time, injecting, in a pulsed manner, an amount of additional buffer liquid into the vessel, with said at least one second closable inlet nozzle being opened, of the mechanical selection unit through the structure of microchannels, to push the initial nematode population towards the open double grid so that members of the initial population having lowest specific weight and specific size smaller than size of the holes of the open double grid pass through the double grid;

closing the double grid and the at least one first and at least one second closable inlet nozzles, whereby the collection vessel contains an intermediate amount of maintenance buffer liquid containing an intermediate population of nematodes a majority of which is in adult stage; opening the closable outlet hole and injecting the intermediate amount of liquid into the optical selection unit through the connection channel with at least three way branch, so as to individually channel nematodes into the at least three measurement microfluidic channels;

optically selecting individual channelled nematodes, optical selection including the following sub-steps:

optically measuring a length/of an individual channelled nematode and checking if the length/is included in a determined range of lengths Δl, wherein if the length l is not included in the determined range Δl, discarding the individual channelled nematode at the output of the at least three measuring channels towards the waste tank;

measuring the green autofluorescence $F_{green}$ and the red autofluorescence $F_{red}$ of the individual channelled nematode and checking if the ratio $$\Delta\left(\frac{F_{green}}{F_{red}}\right)$$

is lower than a determined threshold s, wherein if the ratio $$\Delta\left(\frac{F_{green}}{F_{red}}\right)$$

is greater than the threshold ε, discarding the individual channelled nematode at the output of the at least three measuring channels towards the waste tank;

in the case where the length l is within the range Δl and ratio $$\Delta\left(\frac{F_{green}}{\text{red}}\right)$$

is lower than the determined threshold ε, sending the individual channelled nematode to the pillar microfluidic circuit of the measuring unit towards the loading microchannel and the loading hole and counting nematode number N sent to the measuring unit;

checking if N is equal to or greater than a determined value $N_{tot}$, wherein if the number N is equal to or greater than $N_{tot}$ blocking the passage of nematodes in the measuring unit by activating the blocking valve;

analysing the response of the N nematodes in the pillar microfluidic circuit to an odorant substance through the sub-steps of:

- illuminating an area of the pillar microfluidic circuit with light emitted by the sources of the first end layer;
- measuring a first autofluorescence signal integrated over the area of the pillar microfluidic circuit through the photodiodes associated with the sources to obtain a fluorescence background value and acquiring transmitted light images through the, sCMOS or CCD, optical sensor of the area of the pillar microfluidic circuit to check number and motility of the nematodes in the microfluidic circuit;
- injecting test liquid possibly containing at least one odorant from a third tank into the chip;
- injecting neutral buffer liquid from a fourth tank into the chip to drain the test liquid to the outlet tank;
- measuring a second integrated fluorescence signal through the photodiodes associated with the light sources of the first end layer;
- calculating parameters of the second fluorescence signal, such as rise time $\tau_{rise}$ and fall time $\tau_{fall}$;
- checking if $\tau_{rise}$ is included in a first time range $T_1$, $\tau_{rise} \in T_1$, and $\tau_{fall}$ is included in a second time range $T_2$, $\tau_{fall} \in T_2$, where $T_1$ and $T_2$ are standard time ranges of the rearrangement of calcium concentrations in a neuron activated by the lack of a stimulus sensed by a nematode in presence of an odorant substance, wherein if $\tau_{rise} \notin T_1$ and $\tau_{fall} \notin T_2$, the method recognizes that no odorant substances are present in the test liquid, while if $\tau_{rise} \in T_1$ and $\tau_{fall} \in T_2$, the method checks if there is motility of nematodes due to chemotaxis;
- acquiring transmitted light images through the sCMOS or CCD optical sensor of the area of the microfluidic circuit;
- analysing the acquired images to determine motility of nematodes for checking if there is motility due to chemotaxis, wherein
- if there is no motility due to chemotaxis the method recognizes that no odorant substances are present in the test liquid, while
- if there is motility due to chemotaxis, the method recognizes that odorant substances are present in the test liquid;
- draining the neutral buffer liquid from the chip into the outlet tank.

According to a further aspect of the invention, said step of analysing the N nematode response may be performed for m times, with m=1, 2, . . . , optionally equal to 2, before the method ends.

According to an additional aspect of the invention, said length range Δl may range between the distances of the first optical sensor from the second optical sensor and of the first optical sensor from the third optical sensor respectively, optionally ranging from 900 μm to 1000 μm.

According to another aspect of the invention, said threshold s may be equal to 0.5.

According to a further aspect of the invention, said $Al_{tot}$ may range from 20 to 50.

According to an additional aspect of the invention, said step of analysing the acquired images may be performed by comparing subsequent transmission images and through a differential threshold procedure that generates a binary image, whereby a pixel may be associated to a background or to a nematode depending on whether intensity exceeds a determined threshold or not.

The advantages offered by the apparatus according to the invention with respect to the prior art solutions are numerous and significant.

The unit of separation of the nematodes on the basis of their vital stage downstream of the unit of separation thereof by size and specific weight, ensures a highly efficient nematode population for detecting molecular compounds with respect to a heterogeneous population. This has a first advantage that is to overcome the problem of a synchronous rearing of nematodes, for instance by organizing a system of rearing and distributing nematodes that allows to supply multiple measurement laboratories placed at a reasonable distance from the rearing centre making daily deliveries. A second advantage is to increase the reliability of the detection of molecular compounds as the signal/noise ratio in the measurements of the neuronal response of the nematodes to the molecular compounds increases. The unit of measurement of the response to the stimulus of the odorant substance allows a behavioral measurement, i.e. of chemotaxis, and a measurement of neuronal activity, i.e. of calcium imaging. This advantageously increases the reliability of the apparatus, i.e. its sensitivity, in detecting molecular compounds, reducing false positives or negatives. Another significant advantage is that the apparatus is completely automated and provides response times in the order of few minutes, as opposed to what happens today in laboratory tests where selection and preparation take more than one day. A further advantage is that the apparatus is compact and portable and thus extremely versatile. Still a further advantage is that C. Elegans, as raw material, is available in large quantities or alternatively it is possible to produce it in large quantities and at low cost and does not pose any ethical problem.

The present invention will be now described, by way of illustration and not by way of limitation, according to its preferred embodiments, by particularly referring to the Figures of the annexed drawings, in which.

In the Figures, identical reference numerals will be used for alike elements-.

Figure 1:
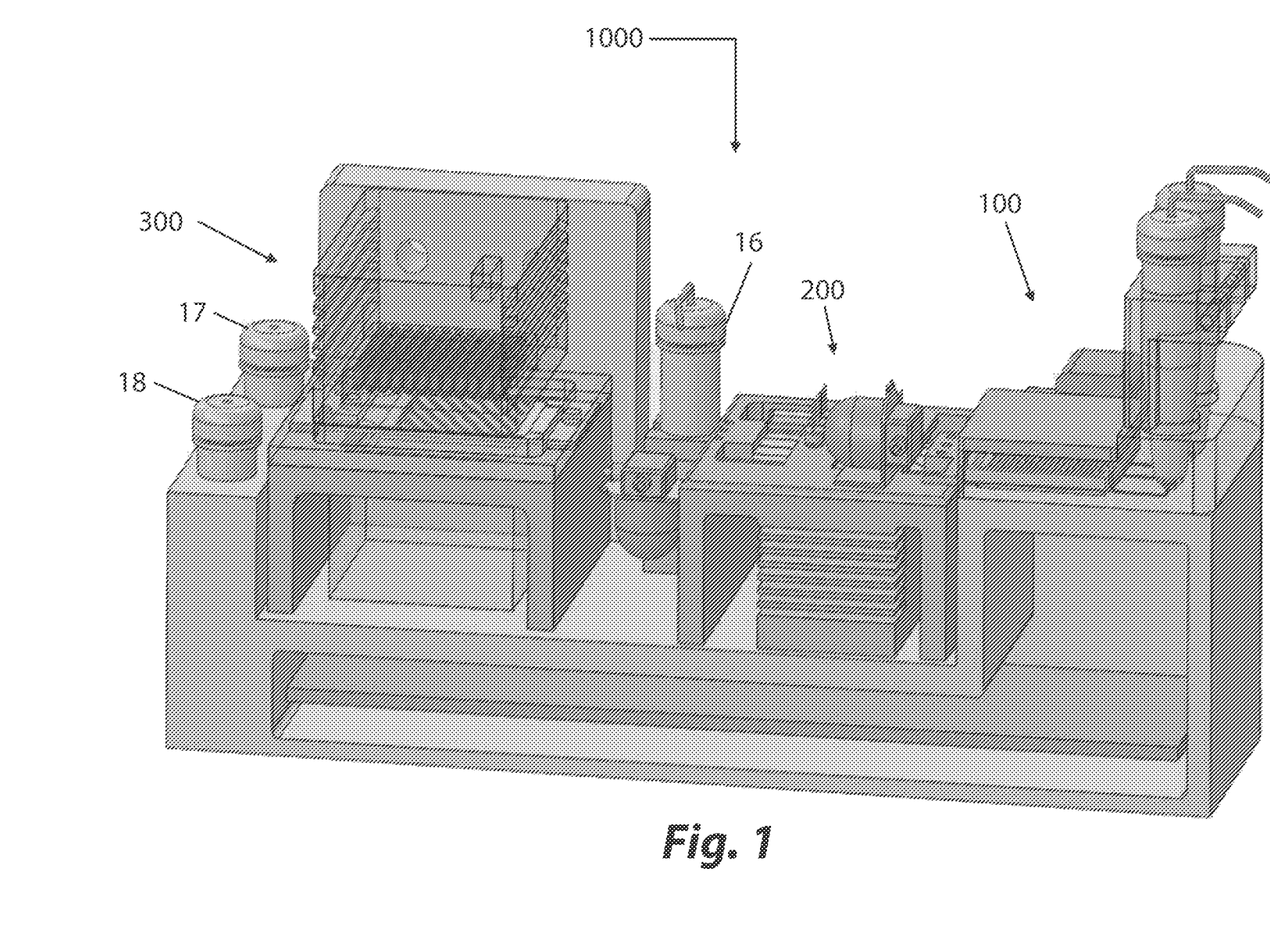
FIG. 1 schematically shows a preferred embodiment of the apparatus according to the invention.
Figure 2:
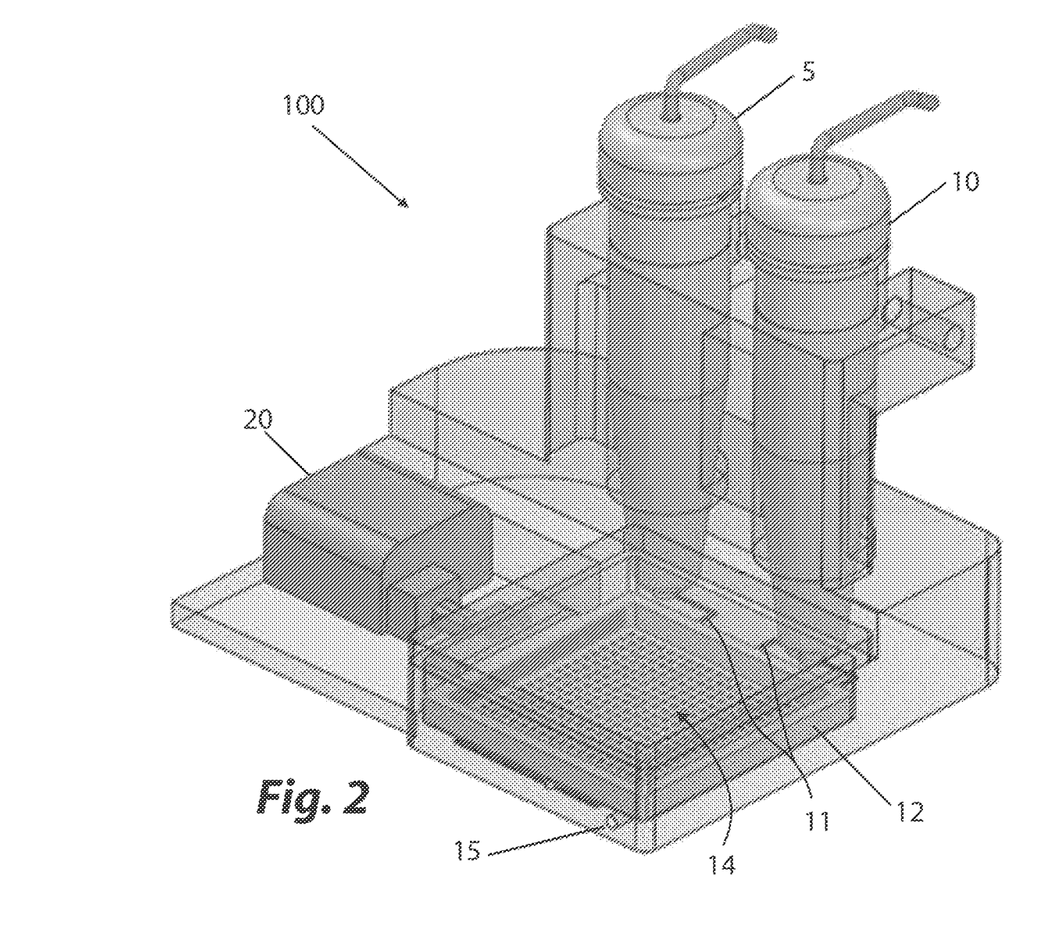
FIG. 2 shows a schematic representation of a unit for mechanical selection of nematodes of the apparatus of FIG. 1.

FIG. 1 shows a preferred embodiment of an apparatus 1000 according to the present invention comprising a unit 100 for mechanical selection of adult nematodes from an initial nematode population to obtain an intermediate nematode population. Such mechanical selection unit 100 is connected to a unit 200 for optical selection of nematodes from the intermediate population to obtain a final population, that is in turn connected to a measurement unit 300 configured to detect the response of nematodes of the final population to a stimulus of an odorant substance. Such first, second and third units will be described in detail in the following with reference to FIGS. 2 to 4. The apparatus 1000 further includes service units for fluid management such as liquid storage tanks and at least one control module (not shown in the Figures) for controlling and regulating flows of liquids, for controlling the mechanical and optical selection units 100, 200 and the measurement unit 300, as well as for analysing data obtained from the measurement unit 300. With reference to FIG. 2, the apparatus 1000 includes a first storage tank 5 for storing *C Elegans* in solution in a maintenance buffer liquid such as for instance M9, S basal, and a second storage tank 10 for storing an additional buffer liquid, i.e. not containing nematodes. The first and second storage tanks 5, 10 are connected at a first end to an overpressure system (not shown in the Figure) operated by a pump and at a second end to an inlet microchannel structure 11. The first microchannel structure 11, of section not lower than 100 μm, optionally equal to 200 μm, connects the first storage tank 5 and the second storage tank 10 to the nematode mechanical selection unit 100. Such inlet microchannel structure 11 has the function of making maintenance buffer liquid containing nematodes or additional buffer liquid pass from the respective storage tanks to the unit 100 through the overpressure system operated by a pump not shown in the Figure. A control unit, not shown in the Figure, controls the pump. The mechanical selection unit 100 is configured to select nematodes in adult stage from an initial nematode population. It comprises a collection vessel 12 provided with a first closable inlet nozzle configured to introduce maintenance buffer liquid containing nematodes into the vessel 12 and a second closable inlet nozzle configured to introduce additional buffer liquid into the vessel 12. The first and second closable inlet nozzles, not shown in the Figure, are positioned on the vessel base and are controlled by the control unit. In other embodiments, the vessel 12 may be provided with more than two closable inlet nozzles.

Figure 3:
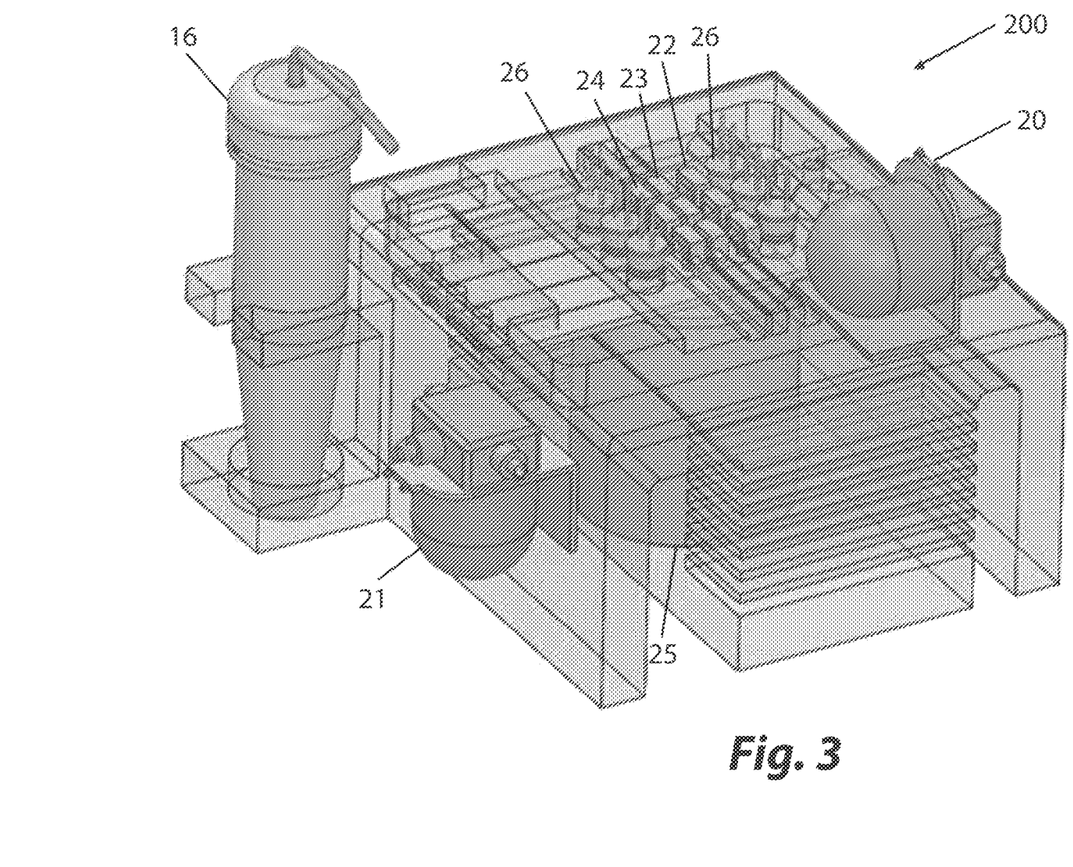
FIG. 3 shows a schematic representation of a unit for optical selection of nematodes of the apparatus of FIG. 1.
Figure 4:
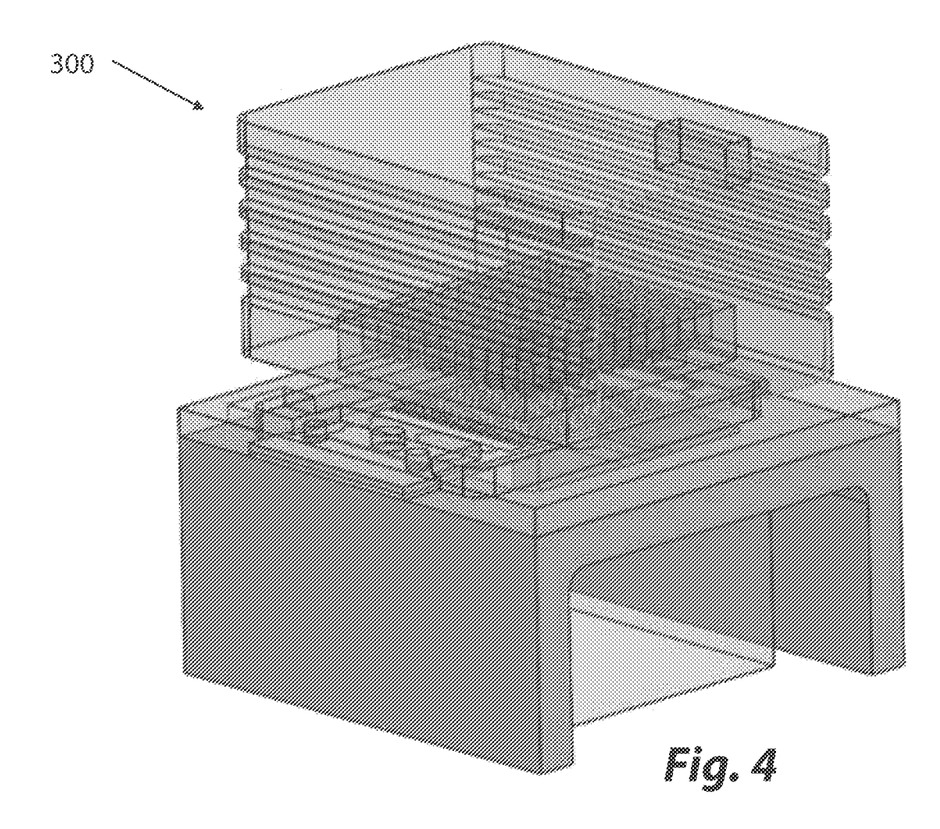
FIG. 4 shows a schematic representation of a unit for measurement of the response of nematodes to a stimulus of an odorant substance of the apparatus of FIG. 1.
Figure 5:
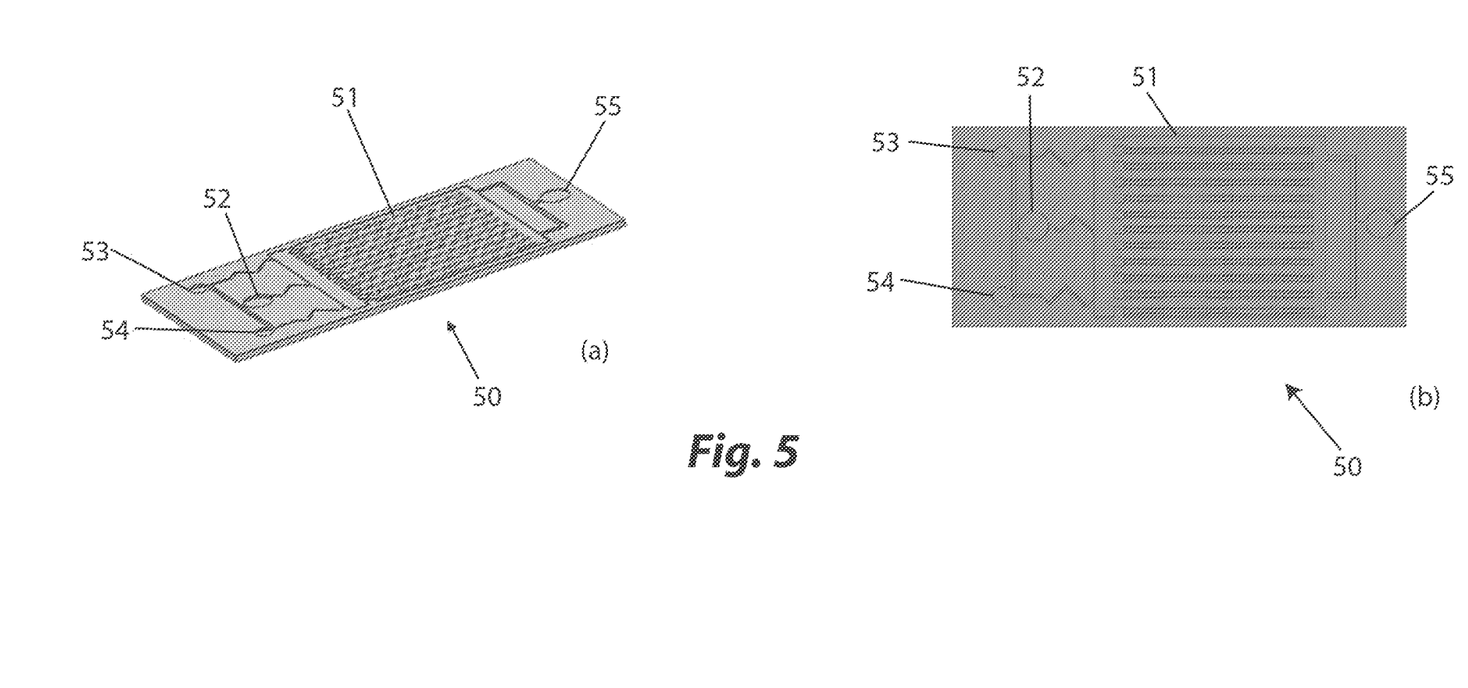
FIG. 5 shows a perspective view (a) and a front view (b) of a microfluidic chip of the apparatus of FIG. 1.
Figure 6:
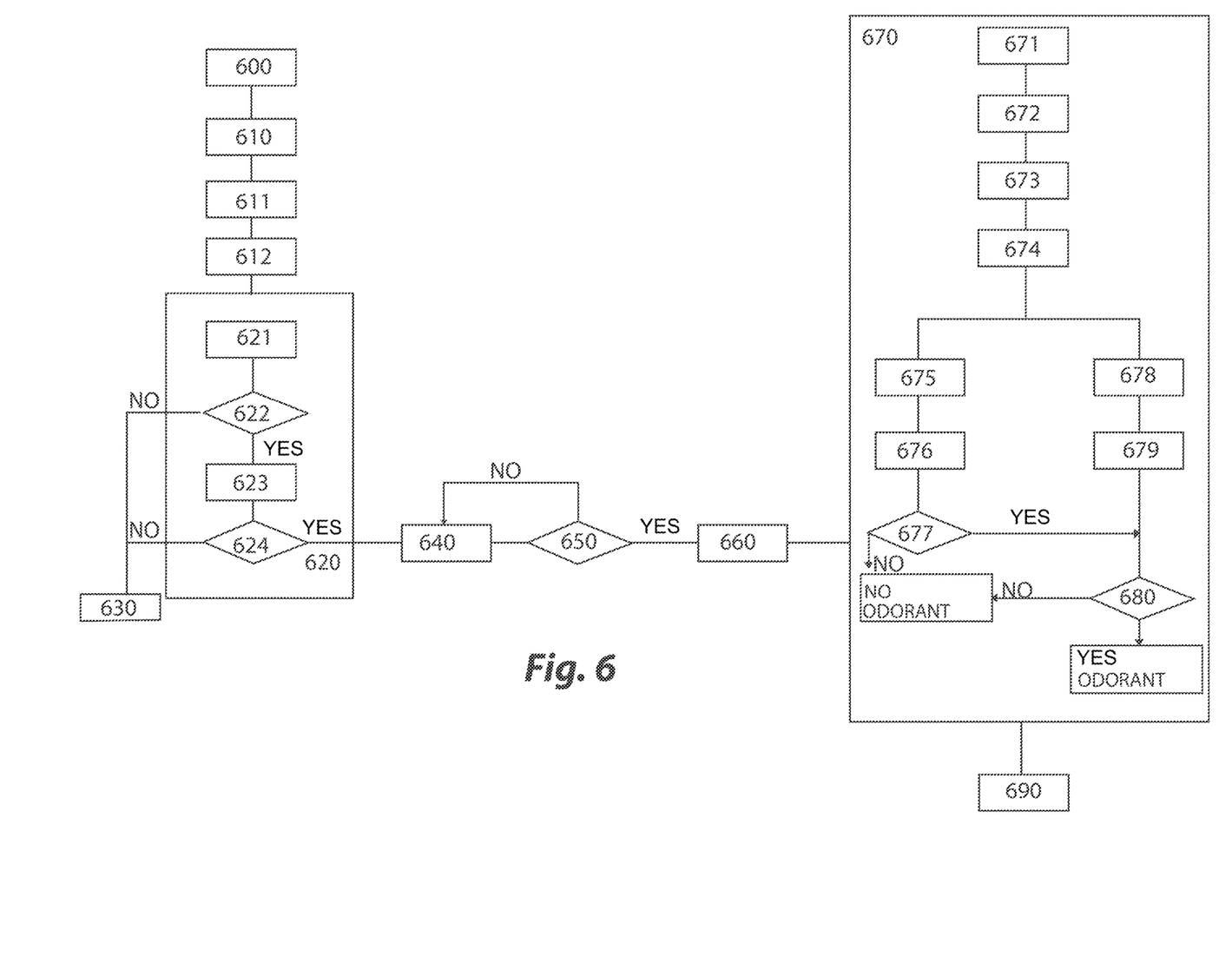
FIG. 6 shows a schematic flow chart of a preferred embodiment of the method according to the invention.

In further embodiments, the at least two nozzles may be placed near a base of the vessel 12. Through the overpressure mechanism operated by the pump controlled by the control unit, an initial amount of maintenance buffer liquid, containing an initial nematode population, is drained from the first storage tank 5, is caused to pass into the inlet microchannel structure 11 and is injected into the collection vessel 12 through the open first closable inlet nozzle. The vessel 12 is sized such that its capacity is greater than the initial amount of liquid drained from the first tank 5. The collection vessel 12 is provided with a double grid 14 placed parallel to the base of the vessel 12 at a certain distance from the same. In the embodiments where the at least two closable inlet nozzles are positioned near the vessel base, the double grid is arranged at a distance from the base greater than the distances of the at least two closable inlet nozzles. The double grid is configured to let only eggs or larvae of nematodes to pass through itself. The double grid 14 is motorised and is controlled by the control unit. The double grid 14 is constituted of a first grid and a second grid parallel thereto. Such first and second grids may translate from each other, through linear actuators 19 so as to assume a first position at which the respective holes are aligned, i.e. the double grid 14 is open, whereby the solution contained in the vessel 12 may pass from inside the vessel 12 outwards through the holes, and a second position at which the respective holes are misaligned, i.e. the double grid 14 is closed, whereby the solution contained in the vessel 12 cannot pass through the holes. In other embodiments of the present invention, the first perforated grid is fixed and a second sliding grid, operated by a linear actuator, opens and closes the double grid 14. It is a square array one with holes which can range from 50 μm to 500 μm. In other embodiments, the holes may assume different shapes from the square. The double grid 14 is placed at a touching height of the vessel 12 so as to touch a liquid volume equal to the volume of the initial amount of maintenance liquid introduced into the vessel 12. Thus, once the initial amount of maintenance liquid is introduced, the double grid 14 touches such liquid amount. When the additional buffer liquid is injected into the vessel 12 containing the initial amount of maintenance liquid, the former pushes the initial nematode population towards the open double grid 14. The additional buffer liquid is designed to make the solution flow from the lower part of the vessel 12 and to push it through the open double grid 14. Thus, the members of the initial population having lowest specific weight and specific size lower than the size of the holes of the open double grid 14, i.e. eggs and larvae, pass through such grid until an intermediate amount of maintenance liquid containing an intermediate nematode population a majority of which is in adult stage remains in the vessel 12. In fact, nematodes in young adult stage, with size (length) in the range 900 940 μm, and in adult stage with size (length) in the range 1110-1150 μm, having size greater than the hole size cannot pass through the open double grid outwards. The vessel 12 includes an outlet hole 15 closable by a first solenoid valve assembly 20, visible in FIG. 3, configured to make liquids exit from the vessel 12 emptying the same. In the preferred embodiment of the invention, the amount of injected solution is of about 200 μL equal to about 200 mm$^3$ of volume, the vessel 12 has a square base of about 6×6 mm$^2$, wherein the double grid 14 is positioned at a height of about 6 mm, so as to touch the amount of initial solution in the vessel 12. In another preferred embodiment, the vessel 12 has a square or rectangular base of greater area, so as to have the double grid 14 positioned at a lower height, closer to the lower part of the vessel 12, with a greater area that can be more easily made. The vessel extends above the grid for a height of additional 11 mm to contain about 400 μL of additional buffer liquid. Other embodiments have different size of the apparatus, whereby the amount of injected solution may be lower or greater than 200 μL depending on the apparatus size. The mechanical selection unit 100 is connected to a unit 200 of optical selection of nematodes via a connection channel with a three way branch not shown in the Figures, each one of section not lower than 100 μm, connected through the first solenoid valve assembly 20 to the closable outlet hole 15 of the vessel 14. In further embodiments, the connection channel may have a branch with a number of ways larger than three. The connection channel has the function of making the intermediate amount of liquid, i.e. the intermediate nematode population a majority of which is in adult stage, pass from the mechanical selection unit 100 to the nematode optical selection unit 200, shown in FIG. 3, through the overpressure mechanism operated by the pump controlled by the control unit, after that said control unit has closed the first and second closable inlet nozzles and the double grid 14. The optical selection unit 200 is configured to select a final population of nematodes in adult stage from the intermediate population and to select nematodes in young adult stage from nematodes in egg producing adult stage, through a first optical measurement and a second optical measurement on each individual nematode contained in the intermediate population. The optical selection unit 200 includes three measurement microfluidic channels, parallel to each other, in which the three way connection channel branches and in which the nematodes are channelled one by one, through the overpressure system operated by a pump. The presence of at least three measurement microfluidic channels avoids possible apparatus operation interruptions caused by nematode blocks in one of the channels themselves. In further embodiments, the number of measurement channels of the optical selection unit is larger than three. During the passage of a nematode in one of the three measurement microfluidic channels, a first and a second optical measurements are performed to ascertain the nematode vital stage. The first optical measurement identifies the length of a channelled nematode and the second optical measurement identifies the green autofluorescence intensity thereof with respect to the red autofluorescence. In fact, once the nematode length is known, it is possible to select nematodes in young adult stage from those in egg producing adult stage. Instead, the measurement of the ratio of the green and red autofluorescences selects nematodes since the ratio of the autofluorescences increases as the nematode age increases. Depending on the results of the performed first and a second optical measurements, nematodes to be sent to the unit 300 of measurement of their response to a stimulus of an odorant substance are selected. The optical selection unit 200 includes a first optical sensor 22, a second optical sensor 23 and a third optical sensor 24 for each one of the three measurement microfluidic channels to perform the first optical measurement of the nematode length. For each measurement channel, the first, second and third optical sensors 22, 23 and 24 are positioned at a first height from the channel and along the longitudinal direction of the channel and they are translated from each other so that the orthogonal projection of the first optical sensor 22 on the related channel identifies a first target position, the orthogonal projection of the second optical sensor 23 on the related channel identifies a second target position and the orthogonal projection of the third optical sensor 24 on the related channel identifies a third target position. In the preferred embodiment of the apparatus, the distances of the second and third optical sensors from the first one are equal to about 900 μm and 1000 μm, respectively. The three optical sensors 22, 23 and 24 are controlled by the control unit. For each one of the three measurement microfluidic channels, the logic of selection of nematodes given by the first optical measurement, and illustrated in the following, provides that, once the first sensor 22 is activated due to the arrival of an individual channelled nematode at the first target position, the electrical signal from the first optical sensor 22 must not fall down to zero until the activation of the second optical sensor 23 caused by the individual channelled nematode when reaching the second target position and it must be back to zero before the activation of the third optical sensor 24 caused by the individual channelled nematode when reaching the second target position. Only when these conditions occur, i.e. when the individual channelled nematode under measurement has a length ranging from a first length identified by the distance between first and second target positions to a second length identified by the distance between first and third target positions and that is attributable to the length of a young adult, the individual channelled nematode is selectable from the intermediate population exiting from the mechanical selection unit 100. The optical selection unit 200 includes an illuminator 25, optionally a LED one, having white light or blue light within the wavelength range 400- 440 nm, configured to illuminate the three measurement microfluidic channels and associated with a double photodiode 26 for each one of the measurement microfluidic channels configured to perform the second optical measurement of autofluorescence of the channelled nematodes. The double photodiode 26 has two sensing elements for detection of light in the green and red wavelengths respectively, two interferential filters deposited on the surface of the sensing elements and two collection optics focusing the emitted light onto each one of the two sensing elements. The nematode selection logic given by the second optical measurement, and illustrated in the following, provides that the ratio between green autofluorescence to red one is lower than a determined threshold, optionally lower than 0.5. Only when this condition and the condition on the length described above occur, the individual channelled nematode is selected from the intermediate population exiting from the mechanical selection unit 100 in a final population. The illuminator 25 is positioned at a second height from the three measurement microfluidic channels. In the preferred embodiment of the invention of FIG. 3, the second height is opposite to the first height of the three optical sensors 22, 23 and 24 and the illuminator 25 is in such a position to perform the second optical measurement of autofluorescence when the nematode is in a central position with respect to the three targets, optionally centrally with respect to the first and second targets. The optical sensors 22, 23 and 24 are controlled by the control unit. In other embodiments, the second measurement of fluorescence is performed in cascade, after the first length measurement. A second solenoid valve assembly 21, controlled by the control unit, is positioned at the outlet of the three measurement microfluidic channels to direct a channelled nematode into a loading microchannel connecting the optical selection unit 200 to the measurement unit 300, optionally with diameter not lower than about 100 μm, towards the measurement unit 300 or towards a waste tank 16. An additional counting optical sensor is positioned in correspondence of the nematode loading microchannel and controlled by the control unit. The apparatus 1000 includes a blocking valve to block the passage of nematodes in the measurement unit 300 after the passage of a determined number of nematodes, optionally ranging from 20 to 50. The nematodes of the intermediate population blocked by the blocking valve remain, for times in the order of few minutes, in the loading channel between the unit 200 and the unit 300 awaiting the next measurement performed by the measurement unit 300 or are sent to the waste tank 16 though the second solenoid valve assembly 21. A schematic representation of the unit 300 of measurement of the response of nematodes to the stimulus of an odorant substance is shown in FIG. 4. The measurement unit 300 is configured to detect the response of nematodes to a stimulus of an odorant substance through measurements of chemotaxis and neuronal activity, i.e. of motility and fluorescence. The measurement unit 300 includes an at least three layer device. A central layer contains a microfluidic chip 50 in which a pillar microfluidic circuit 51 is made, in which wherein nematodes of the final population are introduced. FIG. 5 shows an embodiment of a microfluidic chip 50. Near a first edge of the pillar microfluidic circuit 51, the microfluidic chip 50 is provided with a loading hole 52, connected to the loading microchannel, configured to introduce nematodes into the microfluidic circuit 51. Near the first edge, the microfluidic chip 50 is further provided with a first inlet hole 53 configured to receive a test liquid from a third storage tank 17 through a first inlet channel and with a second inlet hole 54 configured to receive a neutral buffer liquid from a fourth storage tank 18 through a second inlet channel. The test liquid is a liquid in which possible presence of odorant substances has to be detected, and the buffer liquid is a liquid that does not contain odorant substances, such as for instance M9, S basal. Near a second edge of the pillar microfluidic circuit, opposite to the first edge, the microfluidic chip 50 is provided with a drain hole 55, connected to the waste tank 16 through an outlet channel, configured to make liquids exit from the circuit 51. In further embodiments the outlet channel is connected to an outlet tank different from the waste tank 16. In the preferred embodiment of the apparatus according to the invention, the microfluidic chip has size up to 20 mm×20 mm with pillars being 70 µm high, with diameter of 200 µm and spacing of 300 µm, and the liquid inlet channels have a diameter of about 100 µm. Further embodiments of the present invention may have different size and spacing. A first end layer contains continuous light sources and modulated light sources illuminating the microfluidic chip of the central layer and a second end layer (opposite to the first end layer with respect to the central layer) containing an optical sensor such as for instance a sCMOS or CCD to acquire the transmitted light image of the microfluidic chip upon illumination coming from the light sources of the first end layer, i.e. measurement of transmitted light imaging, configured to measure chemotaxis. In particular, to obtain chemotaxis measurements, after that the test liquid has been injected into the worm loading microchannel, the images of the shades obtained by comparing subsequent images are analysed. In the preferred embodiment of the apparatus, the distance between the optical sensor of the second end layer and the chip of the layer is about 300 µm. In the preferred embodiment of the apparatus, the light sources of the first end layer are LEDs arranged in a double array and are configured to emit continuous light at 550 nm, to acquire transmission images, i.e. measurements of transmitted light imaging, and modulated light at 470 nm, optionally with a modulation frequency not exceeding 1 KHz, to stimulate the fluorescence of the green fluorescent protein, GFP, expressed by the particular transgenic nematode line that is employed. In other embodiments of the apparatus, the continuous light sources may be lamps or LEDs emitting white light. The third unit 300 of measurement of response further comprises photodiodes, with proper collection optics, associated with the modulated light sources, on the sensing surfaces of which an interferential filter at about 525/50 nm is deposited that corresponds to the emission peak of the specific GFP of the employed transgenic line. In fact, following appropriate genetic modifications, employed nematodes express a specific protein binding calcium in the receptor neurons. With reference to the flow chart shown in FIG. 6, the steps of a preferred embodiment of the method for automatically detecting odorant substances in a test liquid based on use of nematodes according to the present invention is described in the following. Such method is performed through the use of the apparatus 1000 described above. In an initial step 600, through the overpressure system operated by a pump, an initial amount of maintenance buffer liquid, containing an initial nematode population, is drained from the first storage tank 5 and injected into the mechanical selection unit 100 to select adult nematodes from the initial population. The initial nematode population is injected through the inlet microchannel structure 11 into the collection vessel 12 with the first closable inlet nozzle that is open. The initial amount corresponds to a liquid volume that, when contained in the collection vessel 12, touches the open double grid 14. After a determined interval of time in the order of few minutes, optionally equal to 1 minute, in step 610 amounts of additional buffer liquid, not containing nematodes, are drained in a pulsed manner from the second storage tank 10 through the overpressure system operated by a pump and they are injected into the collection vessel 12 through the inlet microchannel structure 11 with the second closable inlet nozzle that is open. In this way, the additional buffer liquid pushes the initial amount of liquid contained in the vessel 12 through the open double grid 14, so that nematode eggs and larvae pass through the double grid 14. In the execution of the method with the use of the preferred embodiment of the apparatus of the present invention, the number of pulses is 4 and the volumetric flow rate of the amounts of additional buffer liquid is equal to about 100 µL/s. In other embodiments the number of pulses and the volumetric flow rate of the additional buffer liquid may vary depending on the size of the mechanical selection unit 100, in particular on that of the collection vessel 12. At the end of the pulses, in step 611, the double grid 14 is closed to avoid the downfall of the members which have just passed through the double grid 14 and the first and second inlet nozzles of the collection vessel 12 are closed. Thus, the collection vessel 12 contains an intermediate amount of maintenance liquid containing an intermediate nematode population a majority of which is in adult stage. In subsequent step 612, the first solenoid valve assembly 20 opens the closable outlet hole 15 and the intermediate amount of liquid is injected, by means of the overpressure system operated by a pump, through the connection channel with three way branch into the optical selection unit 200, where nematodes of the intermediate population are channelled one by one into the three measurement microfluidic channels. In subsequent step 620, nematodes in adult stage and nematodes in young adult stage are optically selected from the nematodes in egg producing adult stage. Such selection occurs by optically analysing the individual nematodes contained in the intermediate population. Step 620 of optical selection of the nematodes includes two optical measurements 621 and 623 which may be performed simultaneously or in cascade. In sub-step 621, a length l of an individual channelled nematode is optically measured, as previously described, and in sub-step 622 it is checked whether such length/is included within a determined range of lengths Δl. If the length l is not included in the determined range Δl, flow continues through the "NO" branch to step 630 of discarding the nematode, whereby at the outlet of the measurement channels of the optical selection unit 200 the second solenoid valve assembly 21 directs the individual channelled nematode towards the waste tank 16. If the length l is included in the determined range Δl, flows continues through the "YES" branch to sub-step 623 wherein the green autofluorescence $F_{green}$ and the red autofluorescence Fred of the individual channelled nematode are measured, as previously described, and in sub-step 624 it is checked whether the ratio between the green autofluorescence $F_{green}$ and the red one $F_{red}$, $$\Delta\left(\frac{F_{green}}{F_{red}}\right)$$

is lower than a determined threshold s, optionally equal to 0.5. If the ratio $$\Delta\left(\frac{F_{green}}{F_{red}}\right)$$

is greater than the threshold ε, flow continues through the "NO" branch to discarding step 630. If the ratio $$\Delta\left(\frac{F_{green}}{F_{red}}\right)$$

is lower than or equal to the threshold ε, flow continues through the "YES" branch towards subsequent step 640 of sending the individual channelled nematode to the measurement unit 300, whereby, at the outlet of the measurement channels of the optical selection unit 200, the second solenoid valve assembly 21 directs the individual channelled nematode into the loading microchannel towards the microfluidic chip 50 of the measurement unit 300. In step 640, the individual nematodes sent to the measurement unit 300 are further counted by means of the counting optical sensor positioned in correspondence of the nematode loading microchannel, obtaining a number N of sent nematodes. In subsequent step 650, it is checked whether the number N of nematodes sent to the measurement unit 300, measured in step 640, is equal to or larger than a determined value $N_{tot}$, optionally ranging from 20 to 50. If the number N of nematodes sent to the measurement unit 300 is lower than $N_{tot}$, flow continues through the "NO" branch returning to step 640. If the number N of nematodes sent to the measurement unit 300 is equal to or larger than $N_{tot}$, flow continues through the "YES" branch to step 660 of blocking the passage of nematodes in the measurement unit 300 by means of the blocking valve and to subsequent step 670 of analysing the response of the $N_{tot}$ nematodes to an odorant substance in the response measurement unit 300. The analysis 670 of the response of the nematodes to an odorant substance includes the sub-steps described in the following. Initially, in sub-step 671 an area of the pillar microfluidic circuit 51 is illuminated with the light emitted by the sources of the first end layer and in sub-step 672 a first autofluorescence signal integrated over the area of the pillar microfluidic circuit 51 is measured, by means of the photodiodes associated with the sources in order to obtain a background value to use in the analysis of the subsequent fluorescence measurements. In sub-step 672, the positions of the individual nematodes are further stored through measurements of transmitted light imaging, and their number and motility are checked in order to ensure the measurement quality. In sub-step 673, the test liquid is injected from the third tank 17 into the microfluidic chip 50 and in subsequent sub-step 674 the neutral buffer liquid is injected from the fourth tank 18 into the microfluidic chip 50. The injection of neutral buffer liquid into the pillar microfluidic circuit 51 causes the test liquid to be drained from the chip into the waste tank 16 and to be replaced by the neutral buffer liquid itself. In sub-step 675, a second integrated fluorescence signal, i.e. the neuronal signal of the nematodes, is detected by the photodiodes associated with the light sources synchronously with the modulated light sources, with techniques such as for instance the lock-in technique that increases the measurement sensitivity. In sub-step 676, parameters of the neuronal signal such as rise time $\tau_{rise}$ and fall time $\tau_{fall}$ are calculated and in sub-step 677 it is checked whether the time plot of the integrated second fluorescence signal corresponds to a pulse with a rise time included in a first time range $T_1$ and a fall time included in a second time range $T_2$. Such first and second time ranges $T_1$ and $T_2$ are standard ones of the rearrangement of calcium concentrations in a neuron activated by the lack of a stimulus previously sensed by a nematode and their values depend on the particular calcium indicator that is used, respectively in the order of hundreds of milliseconds and of seconds. If $\tau_{rise} \in T_1$ and $\tau_{fall} 531\ T_2$, the method according to the invention recognises that no odorant substance is present in the test liquid and flow continues through the "NO" branch from step 677 to step 690 of the method wherein the neutral buffer liquid is drained from the microfluidic circuit 51 to the outlet tank. If $\tau_{rise} \in T_1$ and $\tau_{fall} \in T_2$, flow continues through the "YES" branch from step 677 to step 680, described in the following, of checking motility due to chemotaxis of the nematodes.

Subsequently to sub-step 674 and simultaneously to sub-step 675, in sub-step 678 transmission images of the area of the pillar microfluidic circuit 51 are acquired by means of the optical sensor, i.e. sCMOS or CCD, of the second end layer of the measurement unit 300. In sub-step 679, the acquired images are analysed to check in sub-step 680 the possible motility due to chemotaxis of the nematodes, whereby if there is motility due to chemotaxis the method recognises that an odorant substance is present in the test liquid, while if the nematodes remain indifferent, i.e. in absence of motility due to chemotaxis, the method recognises that no odorant substance is present in the test liquid. In the case where in step 677 it is ascertained that $T_{rise} \in T_1$ and $\tau_{fall} \in T_2$ and in step 680 absence of motility due to chemotaxis is ascertained, the meethod recognises that it is a false positive. In the preferred embodiment, the analysis of sub-step 679 is performed through worm-tracing techniques, whereby the images of the obtained shades are analysed, i.e. subsequent transmission images are compared. With this technique, the shape of nematodes is then extrapolated from the background noise with a differential threshold procedure between different images both to improve the signal to noise ratio and to discard the fixed background of the microfluidic chip. Such a procedure allows to optimise the video quality so that the nematodes may be easily recognised as highly contrasted (black) objects on a white background. The differential threshold operation described above assigns a pixel to the nematodes or to the background depending on whether the intensity exceeds a determined threshold thus generating a binary image permitting to define the nematode from the head to the tail end. Having this binary image available, it is thus possible to obtain different parameters as the number of nematodes or the centre of mass of the nematodes from which it is then possible to also obtain their speed as rate of displacement of the centre of mass along time. At the end of checking 680 the motility due to chemotaxis, flow continues towards step 690 wherein the neutral buffer liquid is drained from the chip in the outlet tank. In the preferred embodiment of the method, step 670 is performed for m times, with m=1, 2, . . . before that the method ends, i.e. from step 690 of the method flow returns to step 670 for m times before that the method ends. In the preferred embodiment, m=2, the flow rate of the liquids is about $$50 \frac{\mu L}{\min} - 100 \frac{\mu L}{\min},$$

and test liquid is inlet for 30 seconds and neutral buffer liquid is inlet for 30 seconds. With the size of the preferred embodiment of the method, in about 3 seconds a flow rate of 50 μL per minute permits to completely change the content of the pillar microfluidic circuit 51, then to pass from test liquid to neutral buffer liquid, or alternatively to change test liquid.

The preferred embodiments of this invention have been described and a number of variations have been suggested hereinbefore, but it should be understood that those skilled in the art can make other variations and changes without so departing from the scope of protection thereof, as defined by the attached claims.

The invention claimed is:

1. Automated apparatus for detection of odorant substances based on use of nematodes that includes a mechanical selection unit configured to select nematodes in adult stage from an initial nematode population obtaining an intermediate nematode population, a nematode optical selection unit configured to select from the intermediate population a final population of nematodes in adult stage and to select nematodes in young adult stage from nematodes in egg producing adult stage to be sent to a measurement unit configured to detect the response of nematodes of the final population to a stimulus of an odorant substance, the mechanical selection unit being connected to the optical selection unit by a connection channel with an at least three way branch and the optical selection unit being connected to the measurement unit by a loading microchannel, wherein:

the mechanical selection unit comprises a collection vessel provided with at least one first closable inlet nozzle configured to introduce maintenance buffer liquid containing nematodes into the vessel and at least one second closable inlet nozzle configured to introduce additional buffer liquid into the vessel, wherein the vessel is provided with a closable outlet hole and a motorized double grid, configured to assume a first open configuration and a second closed configuration, wherein said at least one first nozzle and said at least one second nozzle being positioned near a base of the vessel and being configured to fill the vessel starting from the base, the motorized double grid being placed parallel to the base of the vessel at a distance from this greater than said at least one first nozzle and said at least one second nozzle and configured to cause only eggs or larvae of nematodes to pass through its own holes;

the optical selection unit comprises at least three measurement microfluidic channels configured to channel one by one nematodes of the intermediate population, three optical sensors configured to perform a length measurement of the channeled nematodes, an illuminator configured to illuminate the at least three measurement microfluidic channels and that is associated to double photodiodes configured to perform an autofluorescence measurement of the individual channeled nematodes, the optical selection unit being configured to direct a nematode towards the measurement unit or towards a waste tank, and a blocking valve configured to block the passage of nematodes in the measurement unit;

the measurement unit comprises a central layer that includes a microfluidic chip with a pillar microfluidic circuit provided with a loading hole connected to the loading microchannel configured to introduce nematodes into the microfluidic circuit and a drain hole configured to remove nematodes from the microfluidic circuit, the chip being configured to receive a test liquid via a first inlet channel and to receive a neutral buffer liquid via a second input channel, a first end layer including sources configured to emit continuous light and modulated light illuminating the microfluidic circuit, the emitted modulated light being configured to stimulate a fluorescence of nematodes, and the sources being associated with photodiodes configured to receive fluorescence of nematodes, a second end layer including an optical sensor opposite to the first end layer with respect to the central layer, configured to acquire transmitted light images of the microfluidic circuit when it is illuminated by the emitted continuous light and to analyze motility nematodes in presence and in absence of an odorant substance;

the apparatus further comprising a control unit for controlling the mechanical selection unit, the optical selection unit and the measurement unit.

2. Apparatus according to claim 1, wherein the at least three ways of the connection channel and the loading microchannel have a section not lower than 100 μm.

3. Apparatus according to claim 1, wherein the holes of the double grid have a size ranging from 50 μm to 500 μm.

4. Apparatus according to claim 1, wherein for each of the at least three measurement microfluidic channels the three optical sensors are positioned along a longitudinal direction of the channel and are translated from each other at such distances that orthogonal projections on the channel of a first optical sensor, of a second optical sensor and of a third optical sensor identify a first target position, a second target position and a third target position respectively.

5. Apparatus according to claim 4, wherein, with respect to each of the at least three measurement microfluidic channels, each optical sensor is positioned at a first height and the illuminator at a second height opposite to the first height, the illuminator being positioned in a central position with respect to the three target positions.

6. Apparatus according to claim 1, wherein the sources of the first end layer are LEDs arranged in a double array to emit continuous light and modulated light.

7. Method for automatically detecting odorant substances based on use of nematodes employing an automated apparatus for detection of odorant substances based on use of nematodes that includes a mechanical selection unit configured to select nematodes in adult stage from an initial nematode population obtaining an intermediate nematode population, a nematode optical selection unit configured to select from the intermediate population a final population of nematodes in adult stage and to select nematodes in young adult stage from nematodes in egg producing adult stage to be sent to a measurement unit configured to detect the response of nematodes of the final population to a stimulus of an odorant substance, the mechanical selection unit being connected to the optical selection unit by a connection channel with an at least three way branch and the optical selection unit being connected to the measurement unit by a loading microchannel, wherein:

the mechanical selection unit comprises a collection vessel provided with at least one first closable inlet nozzle configured to introduce maintenance buffer liquid containing nematodes into the vessel and at least one second closable inlet nozzle configured to introduce additional buffer liquid into the vessel, wherein the vessel is provided with a closable outlet hole and a motorized double grid, configured to assume a first open configuration and a second closed configuration, wherein said at least one first nozzle and said at least one second nozzle being positioned near a base of the vessel and being configured to fill the vessel starting from the base, the motorized double grid being placed parallel to the base of the vessel at a distance from this greater than said at least one first nozzle and said at least one second nozzle and configured to cause only eggs or larvae of nematodes to pass through its own holes;

the optical selection unit comprises at least three measurement microfluidic channels configured to channel one by one nematodes of the intermediate population, three optical sensors configured to perform a length measurement of the channeled nematodes, an illuminator configured to illuminate the at least three measurement microfluidic channels and that is associated to double photodiodes configured to perform an autofluorescence measurement of the individual channeled nematodes, the optical selection unit being configured to direct a nematode towards the measurement unit or towards a waste tank, and a blocking valve configured to block the passage of nematodes in the measurement unit;

the measurement unit comprises a central layer that includes a microfluidic chip with a pillar microfluidic circuit provided with a loading hole connected to the loading microchannel configured to introduce nematodes into the microfluidic circuit and a drain hole configured to remove nematodes from the microfluidic circuit, the chip being configured to receive a test liquid via a first inlet channel and to receive a neutral buffer liquid via a second input channel, a first end layer including sources configured to emit continuous light and modulated light illuminating the microfluidic circuit, the emitted modulated light being configured to stimulate a fluorescence of nematodes, and the sources being associated with photodiodes configured to receive fluorescence of nematodes, a second end layer including an optical sensor opposite to the first end layer with respect to the central layer, configured to acquire transmitted light images of the microfluidic circuit when it is illuminated by the emitted continuous light and to analyse motility nematodes in presence and in absence of an odorant substance;

the apparatus further comprising a control unit for controlling the mechanical selection unit, the optical selection unit and the measurement unit, the method comprising the following steps:

injecting an initial amount of maintenance buffer liquid containing an initial population of nematodes into the vessel, with said at least one first closable inlet nozzle being open, of the mechanical selection unit through an overpressure system through a microchannel structure, said initial amount of maintenance buffer liquid being such as to touch the double grid in open configuration;

after an interval of time, injecting, in a pulsed manner, an amount of additional butler liquid into the vessel, with said at least one second closable inlet nozzle being opened, of the mechanical selection unit through the structure of microchannels, to push the initial nematode population towards the open double grid so that members of the initial population having lowest specific weight and specific size smaller than size of the holes of the open double grid pass through the double grid;

closing the double grid and the at least one first and at least one second closable inlet nozzles, whereby the collection vessel contains an intermediate amount of maintenance buffer liquid containing an intermediate population of nematodes a majority of which is in adult stage;

opening the closable outlet hole and injecting the intermediate amount of liquid into the optical selection unit through the connection channel with at least three way branch, so as to individually channel nematodes into the at least three measurement microfluidic channels;

optically selecting individual channeled nematodes, optical selection including the following sub-steps:

optically measuring a length l of an individual channeled nematode and checking if the length l is included in a determined range of lengths $\Delta l$, wherein if the length l is not included in the determined range $\Delta l$, discarding the individual channeled nematode at the output of the at least three measuring channels towards the waste tank;

measuring the green autofluorescence $F_{green}$ and the red autofluorescence $F_{red}$ of the individual channeled nematode and checking if the ratio $$\Delta\left(\frac{F_{green}}{F_{red}}\right)$$

is lower than a determined threshold $\varepsilon$, wherein if the ratio $$\Delta\left(\frac{F_{green}}{F_{red}}\right)$$

is greater than the threshold $\varepsilon$, discarding the individual channeled nematode at the output of the at least three measuring channels towards the waste tank;

in the case where the length l is within the range $\Delta l$ and ratio $$\Delta\left(\frac{F_{green}}{red}\right)$$

is lower than the determined threshold $\varepsilon$, sending the individual channeled nematode to the pillar microfluidic circuit of the measuring unit towards the loading microchannel and the loading hole and counting nematode number N sent to the measuring unit;

checking if N is equal to or greater than a determined value $N_{tot}$, wherein if the number N is equal to or greater than $N_{tot}$ blocking the passage of nematodes in the measuring unit by activating the blocking valve;

analyzing the response of the N nematodes in the pillar microfluidic circuit to an odorant substance through the sub-steps of:

illuminating an area of the pillar microfluidic circuit with light emitted by the sources of the first end layer;

measuring a first autofluorescence signal integrated over the area of the pillar microfluidic circuit through the photodiodes associated with the sources to obtain a fluorescence background value and acquiring transmitted light images through the, sCMOS or CCD, optical sensor of the area of the pillar microfluidic circuit to check number and motility of the nematodes in the microfluidic circuit;

injecting test liquid possibly containing at least one odorant from a third tank into the chip;

injecting neutral buffer liquid from a fourth tank into the chip to drain the test liquid to the outlet tank;

measuring a second integrated fluorescence signal through the photodiodes associated with the light sources of the first end layer;

calculating parameters of the second fluorescence signal, such as rise time $\tau_{rise}$ and fall time $\tau_{fall}$;

checking if $\tau_{rise}$ is included in a first time range $T_1$, $\tau_{rise} \in T_1$, and $\tau_{fall}$ is included in a second time range $T_2$, $\tau_{fall} \in T_2$, where $T_1$ and $T_2$ are standard time ranges of the rearrangement of calcium concentrations in a neuron activated by the lack of a stimulus sensed by a nematode in presence of an odorant substance, wherein if $\tau_{rise} \notin T_1$ and $\tau_{fall} \notin T_2$, the method recognizes that no odorant substances are present in the test liquid, while if $\tau_{rise} \in T_1$ and $\tau_{fall} \in T_2$, the method checks if there is motility of nematodes due to chemotaxis;

acquiring transmitted light images through the sCMOS or CCD optical sensor of the area of the microfluidic circuit;

analyzing the acquired images to determine motility of nematodes for checking if there is motility due to chemotaxis, wherein if there is no motility due to chemotaxis the method recognizes that no odorant substances are present in the test liquid, while if there is motility due to chemotaxis, the method recognizes that odorant substances are present in the test liquid;

draining the neutral buffer liquid from the chip into the outlet tank.

8. Method according to claim 7, wherein the step of analyzing the N nematode response is performed for m times, with m=1, 2, . . . , before the method ends.

9. Method according to claim 7, wherein the length range $\Delta l$ ranges between the distances of the first optical sensor from the second optical sensor and of the first optical sensor from the third optical sensor respectively.

10. Method according to claim 7, wherein the threshold $\varepsilon$ is equal to 0.5.

11. Method according to claim 7, wherein $N_{tot}$ ranges from 20 to 50.

12. Method according to claim 7, wherein the step of analyzing the acquired images is performed by comparing subsequent transmission images and through a differential threshold procedure that generates a binary image, whereby a pixel is associated to a background or to a nematode depending on whether intensity exceeds a determined threshold or not.

13. Apparatus according to claim 4, wherein the second and the third optical sensors are translated with respect to the first optical sensor by about 900 µm and 1000 µm respectively.

14. Apparatus according to claim 5, wherein the illuminator is centrally positioned with respect to the first and second target positions.

15. Apparatus according to claim 1, wherein the sources of the first end layer are LEDs arranged in a double array to emit continuous light and modulated light with a modulation frequency not exceeding 1 KHz.

16. Apparatus according to claim 1, wherein the sources of the first end layer are LEDs arranged in a double array to emit continuous light at 550 nm and modulated light at 470 nm.

17. Apparatus according to claim 1, wherein the sources of the first end layer are LEDs arranged in a double array to emit continuous light at 550 nm and modulated light at 470 nm with a modulation frequency not exceeding 1 KHz.

18. Method according to claim 8, wherein the step of analyzing the N nematode response is performed for m=2 times before the method ends.

19. Method according to claim 9, wherein the length range $\Delta l$ ranges from 900 µm to 1000 µm.

* * * * *